(12) United States Patent
Reiter et al.

(10) Patent No.: US 7,524,676 B2
(45) Date of Patent: Apr. 28, 2009

(54) LARGE SCALE PRODUCTIONS OF VIRUS ANTIGEN

(75) Inventors: Manfred Reiter, Vienna (AT); Wolfgang Mundt, Vienna (AT)

(73) Assignee: Baxter Healthcare S.A., Zurich (CH)

( * ) Notice: Subject to any disclaimer, the term of this patent is extended or adjusted under 35 U.S.C. 154(b) by 273 days.

(21) Appl. No.: 11/084,485

(22) Filed: Mar. 17, 2005

(65) Prior Publication Data
US 2005/0181495 A1 Aug. 18, 2005

Related U.S. Application Data

(62) Division of application No. 10/006,881, filed on Dec. 10, 2001, now Pat. No. 6,951,752.

(51) Int. Cl.
*C12N 5/10* (2006.01)
*C12N 7/02* (2006.01)

(52) U.S. Cl. ...................... 435/325; 435/239

(58) Field of Classification Search ................ None
See application file for complete search history.

(56) References Cited

U.S. PATENT DOCUMENTS

| | | | |
|---|---|---|---|
| 4,525,349 A | 6/1985 | Montagnon et al. | |
| 5,719,051 A * | 2/1998 | Mundt et al. | 435/235.1 |
| 5,824,536 A * | 10/1998 | Webster et al. | 435/235.1 |
| 5,994,134 A | 11/1999 | Giroux et al. | |
| 6,048,537 A | 4/2000 | Violay et al. | |
| 6,100,061 A | 8/2000 | Reiter et al. | |
| 6,344,354 B1 | 2/2002 | Webster et al. | |
| 6,455,298 B1 | 9/2002 | Groner et al. | |
| 6,855,535 B2 * | 2/2005 | Meyer et al. | 435/235.1 |
| 6,951,752 B2 * | 10/2005 | Reiter et al. | 435/235.1 |

FOREIGN PATENT DOCUMENTS

| | | | |
|---|---|---|---|
| WO | WO 91/09935 A1 | 7/1991 | |
| WO | WO 96/15231 A1 | 5/1996 | |
| WO | WO98/33886 A1 * | 8/1998 | |

OTHER PUBLICATIONS

C.A.M. van der Velden-de Groot, Cytotechnology, 1995, 18:51-56.*
Barrett et al., "Large-Scale Production and Purification of a Vaccinia Recombinant-Derived HIV-1 gp160 and Analysis of Its Immunogenicity", 1989, *Aids Research and Human Retroviruses* vol. 5, No. 2, pp. 159-172, XP001064669.
Butler; 1988, *Animal Cell Biotechnology*, Ed. R.E. Spier and J.B. Griffiths, vol. 3, pp. 284-303.
Caij Jr. et al.; "High Titre Hog Cholera Virus Production on Cytodex 3® Microcarrier Cultures"; 1989, *Archives of Virology*, vol. 105, pp. 113-118.
Cinati Jr. et al.; "Protein-Free Culture of Vero Cells: A Substrate for Replication of Human Pathogenic Viruses"; 1993, *Cell Biology International*, vol. 17, No. 9, pp. 885-895.

Fiorentine et al.; "production of Herpesvirus of Turkeys in Microcarrier Culturing System—A New Method for Production of Vaccine Against Marek's Disease"; 1985, *Develop Biol. Standard*, vol. 60, pp. 421-430.
Griffiths et al.; "The Development and Use of Microcarrier and Glass Sphere Culture Techniques for the Production of Herpes Simplex Viruses"; 1982, *Develop Biol. Standard*, vol. 50, pp. 103-110.
Holzer et al.; "Construction of a Vaccinia Virus Deficient in the Essential DNA Repair Enzyme Uracil DNA Glycosylase by a Complementing Cell Line"; 1997, *Journal of Virology*, vol. 71, pp. 4997-5002.
Kessler et al.; "Suitability of MDCK Cells Grown in a Serum-Free Medium for Influenza Virus Production"; 1999, *Dev. Biol. Stand.*, vol. 98, pp. 13-21.
Kistner et al.; "Development of a Mammalian Cell (Vero) Derived Candidate Influenza Virus Vaccine"; 1998, *Vaccine*, vol. 16, No. 9/10, pp. 960-968.
Kistner et al.; "Development of a Vero Cell-Derived Influenza Whole Virus Vaccine"; 1999, *Dev. Biol. Stand.*, vol. 98, pp. 101-110.
Kistner et al., "Development of a novel influenza vaccine derived from a continuous cell line!", 2001, *Linz* 18:1: 50-54 XP001146190.
Kistner et al., "Novel Mammalian Cell (Vero) Derived Influezy Virus Vaccine: Development, Characterization and Individual Scale Production", 1999 *Wiener Klinische Wochenschrift*, vol. 111, No. 5, pp. 207-214, XP000909353.
Merten et al.; "Evaluation of the New Serum-Free Medium (MDSS2) for the Production of Different Biologicals: Use of Various Cell Lines"; 1994, *Cytotechnology*, vol. 14, pp. 47-59.
Merten et al.; "Production of Influenza Virus in Serum-Free Mammalian Cell Cultures"; 1999, *Dev. Biol. Stand.*, vol. 98, pp. 23-37.
Miller et al.; "Microbeads and Anchorage-Dependent Eukaryotic Cells: The Beginning of a New Era in Biotechnology"; 1989, *Advances in Biochemical Engineering/Biotechnology*, vol. 39, pp. 73-95.
Percheson et al., "A Phase I, Randomized Controlled Clinical Trial to Study the Reactogenicity and Immunogenicity of a New Split Influenza Vaccine Derived from a Non-Tumorigenic Cell Line", 1999, *Developments in Biological Standardization* 98: 127-132, XP009008177.
Reuveny et al.; "Newly Developed Microcarrier Culturing Systems-An overview"; 1985, *Develop. Biol. Standard*, vol. 60, pp. 243-253.
Sanford et al.; "The Measurement of Proliferation in Tissue Cultures by Enumeration of Cell Nuclei"; 1951, *J. Natl. Cancer Inst.*, vol. 11, pp. 773-795.
Seewoster et al.; "Cell Size Distribution as a Parameter for the Prodetermination of Exponential Growth During Repeated Batch Cultivation of CHO Cells"; 1997, *Biotechnology and Bioengineering*, vol. 55, pp. 793-797.

(Continued)

*Primary Examiner*—Stacy B Chen
(74) *Attorney, Agent, or Firm*—Townsend and Townsend and Crew LLP

(57) ABSTRACT

The present invention provides improved methods of production of viral antigen on a culture of adherent cells bound to a microcarrier, wherein the methods provide for increased viral antigen yield per culture medium volume. The invention is also directed to a cell culture biomass of adherent cells having increased cell density and microcarrier concentration compared to the respective confluent cell culture.

10 Claims, No Drawings

OTHER PUBLICATIONS

Sharkey et al., "Ross River Virus Glycoprotein-Pseudotyped Retroviruses and Stable Cell Lines for Their Production", 2001, *Journal of Virology* 75:6: 2653-2659, XP002235506.

Van Wezel; "Growth of Cell-Strains and Promary Cells on Micro-Carriers in Homogeneous Culture"; 1978, *Process Biochemistry*, vol. 13, pp. 6-8.

Van Wezel et al.; "Large Scale Cultivation of Animal Cells in Microcarrier Culture"; 1978, *Process Biochemistry*, vol. 13, pp. 6-8.

Widell et al.; "A Microcarrier Cell Culture System for Large Scale Production of Hepatitis A Virus"; 1984, *Journal of Virological Methods*, vol. 8, pp. 63-71.

* cited by examiner ant to allow efficient adsorption of virus to the cells. In
LARGE SCALE PRODUCTIONS OF VIRUS ANTIGEN This application is a divisional of U.S. patent application Ser. No. 10/006,881, filed on Dec. 10, 2001, now issued as U.S. Pat. No. 6,951,752.

FIELD OF THE INVENTION

The present invention is directed to improved methods of production of viral antigen on a culture of adherent cells bound to a microcarrier, wherein the methods provide for increased viral antigen yield per culture medium volume. The invention is also directed to a cell culture biomass of adherent cells having increased cell density and microcarrier concentration compared to the respective confluent cell culture.

BACKGROUND OF THE INVENTION

Efficient vaccine production requires the growth of large scale quantities of virus produced in high yields from a host system. The cultivation conditions under which a virus strain is grown is of great significance with respect to achieving an acceptable high yield of the strain. Thus, in order to maximize the yield of the desired virus, both the system and the cultivation conditions must be adapted specifically to provide an environment that is advantageous for the production of the desired virus. Therefore, in order to achieve an acceptably high yield of the various virus strains, a system which provides optimum growth conditions for a large number of different virus is required.

The only process which is economically viable is a reactor process because the scale-up can be made appropriate to the market size and the vaccine doses needed. For adherent cells the carrier process with a classical microcarrier is currently the best choice for large scale cultivation of the cells needed for virus propagation (Van Wezel et al. 1967. Nature 216:64-65; Van Wezel et al. 1978. Process Biochem. 3:6-8). Large-scale process production of poliomyelitis virus, Hepatitis A Virus, HSV or Mareck's disease virus on microcarrier has been described (U.S. Pat. No. 4,525,349; Widell et al., 1984. J. Virological Meth. 8:63-71; Fiorentine et al., 1985. Develop. Biol. Standard 60:421-430; Griffiths et al., 1982. Develop. Biol. Standard. 50:103-110). Current processes based on microcarrier culture allow production of virus using fermenter sizes of up to 1200 l.

Caij et al. (1989. Arch. Virol. 105:113-118) compared production yields of virus titre of Hog Cholera Virus on microcarrier cultures and conventional monolayer cultures and found that using the microcarrier system higher virus yield per volume of medium can be obtained.

Griffiths et al. (1982. Develop. Biol. Standard. 50:103-110) studied the influence of the microcarrier concentration on cell growth and production of HSV. It was found that an optimal concentration of microcarriers is needed to reach high cell density, which also influences the virus yield obtained. Higher concentrations of microcarrier in a perfusion system, however, resulted in a cell loss due to cell layer sloughing off the beads.

The productivity of the virus production process on the microcarrier system depends on the virus, the cells, the type of microcarrier and the cell density obtained in the system. Higher microcarrier concentrations in the cell culture allow for higher total cell numbers. However, microcarriers are costly and, in these conditions, cell loss may occur due to the cell layers sloughing off the beads by the shearing force in the system. This implies that for higher virus yields a larger volume of microcarrier cell culture is needed, but this increases the efforts that have to be made for processing and purification such large volumes.

For virus propagation it is important that optimal cell density is reached to obtain maximal virus yield. It is also important to allow efficient adsorption of virus to the cells. In conventional methods, therefore, the volume of the growth medium is reduced prior to infection to allow adsorption of the virus to the cells in a minimum of culture volume and for a better virus to cells ratio. However, to obtain optimal virus propagation, the culture medium volume is again increased after appropriate adsorption time to allow the cells to maintain viability and/or growth. This, however, increases the culture medium volume comprising cells and/or virus which has the disadvantage that large volumes have to be processed for further purification of the virus from the cells or the cell culture medium.

In the case of an outbreak of a virus infection, it is critical to produce large amounts of a vaccine in a timely fashion to provide several million vaccine doses within a very short period of time. Therefore, a continuing need exists for safe and effective methods to produce viruses and antigens. Moreover, there is a need for an approach to viral propagation, employing materials that are already available and requiring a minimal number of timeconsuming manipulations, such as handling of reduced volumes of cell culture medium and facilitate purification and down stream processing for vaccine production.

BRIEF SUMMARY OF THE INVENTION

It is an object of the present invention to provide for a method for production of virus or viral antigen in a cell culture of adherent cells bound to microcarrier.

It is also an object of the present invention to provide for a method of production of virus in a small cell culture volume.

It is also an object of the present invention to provide for a cell culture of adherent cells having higher cell density compared to the original cell culture grown to confluence.

It is an object of the invention to provide for a cell culture of adherent cells bound to microcarrier and having higher cell density compared to the original cell culture grown to confluence, wherein these cells are infected with virus.

DETAILED DESCRIPTION OF THE INVENTION

In accordance with these and other objects, the present invention provides methods for production of virus or viral antigen, comprising the steps of providing a culture of adherent cells bound to a microcarrier, growing the cell culture to confluence, infecting these cells with a virus, wherein the cell density in the cell culture is increased (i) prior to infection with the virus or (ii) after infection with the virus, and incubating the culture of cells infected with the virus to propagate the virus. The increase of cell density in the cell culture is done by concentration of the cell culture, which includes an increase of microcarrier concentration in the cell culture.

In general, adherent cells bound to microcarriers need an optimal ratio of microcarrier concentration to cells to reach high cell density. The increase of microcarrier concentration in the cell culture theoretically would allow to reach a higher cell density per volume of culture medium. However, due to the shearing effects, reduction of feeding sources in the medium and physiological stress of the cells by increased microcarrier concentration, the carrier concentration in a cell culture system is limited to a specific concentration (see also Griffiths et al. 1982, supra).

The method of the invention allows the cells to grow under optimal growth conditions, including microcarrier concentration, feeding and minimal physiological stress, to reach the maximal cell density for the system used.

In the present invention, it is found that reduction of the culture medium volume prior or after infection with virus, whereby the cell density and microcarrier concentration in the cell culture biomass is increased, does not influence the productivity of the cells. In contrast, it is also surprisingly found that the virus yield obtained per cell can be increased compared to cells that are maintained at the same cell density as the original confluent cell culture. This was highly unexpected as due to the increase of the microcarrier concentration in the cell culture, a reduction of cell viability, sloughing of the cells from the microcarriers and physiological stress due higher cell density and during virus production would have been expected.

The method of the invention allows to reduce the culture medium volume that has to be processed during further purification process of virus, while simultanously the productivity of virus per cell is similar or even increased compared to the original cell culture. The system can be scaled-up to 6000 l fermenter volume, which makes the process for virus production for vaccines more efficiently and time-consuming.

According to one embodiment of the method the anchorage-dependent cells are selected from the group of adherent cells of VERO, BHK, CHO, RK, RK44, RK13, MRC-5, MDCK, CEF or diploid monolayer cells as described by Reuveny et al. (1985. Develop. Biol. Standard. 60:243-253) and others well known in the art.

The adherent cells bound to a microcarrier can be grown in conventional culture medium containing serum. According to a preferred embodiment of the invention the cells are grown in serum free or serum and protein free medium as described by Kistner et al. (1998. Vaccine 16: 960-968), Merten et al. (1994. Cytotech. 14:47-59), Cinatl. et al. (1993. Cell Biology Internat. 17:885-895), Kessler et al. (1999. Dev. Biol. Stand. 98:13-21), WO 96/15231, U.S. Pat. No. 6,100,061 or any other serum free or serum and protein free medium known in the art. The cells are preferably grown from the ampoule to the large scale to the biomass in serum free or serum and protein free medium.

According to one embodiment of the invention the culture of adherent cells bound to a microcarrier are grown to confluence and infected with a virus after increase of cell density and microccarrier concentration of cell biomass of the confluent cell culture.

According to one embodiment of the invention the culture of adherent cells bound to a microcarrier is grown to confluence and infected with a virus prior increase of cell density and microccarrier concentration of the confluent biomass. In any case, if either the cell culture having higher cell density and microcarrier concentration per volume is infected prior or after concentration of the culture, the cell density, microcarrier concentration in the biomass is kept constant during virus propagation and production process, while the volume of the medium is not increased again.

The method used to increase the cell density and microcarrier concentration in the cell culture biomass, either uninfected or infected with a virus, can be any method known in the art to concentrate a cell culture. This can be done by methods like, e.g. sedimentation, centrifugation, filtration, concentration with a perfusion device, like a sieve, that allows the reduction of working volume, or by pooling 2 or more bioreactor systems.

The cell culture density and microcarrier concentration of the cell culture grown to confluence are increased, wherein the increase should be at least 1,3-fold compared to the original biomass grown to confluence. The cell density of the original starting cell culture that has been grown to confluence can be between about $0.6 \times 10^6$ and about $7.0 \times 10^6$ cells/ml. In this case, the biomass having increased cell density compared to the starting culture biomass can have a cell density between at least $0.8 \times 10^6$ and at least $9.0 \times 10^6$ cells/ml.

The microcarrier concentration in the start cell culture is preferably in the range of about 0.5 g/l to about 7.0 g/l. The concentration of the microcarrier after concentration of the confluent biomass is preferably in the range of about 0.65 g/l and about 21 g/.

The microcarrier used according to the method of the invention is preferably selected from the group of microcarriers based on dextran, collagen, polystyrene, polyacrylamide, gelatine, glass, cellulose, polyethylene and plastic and those described by Miller et al. (1989. Advances in Biochem Eng./Biotech. 39:73-95) and described in Butler (1988. In: Spier & Griffiths, Animal cell Biotechnology 3:283-303).

According to one embodiment of the method of the invention the virus is selected from the group of Influenza virus, Ross River Virus, Hepatitis A Virus, Vaccinia Virus and recombinant Vaccinia Virus, Herpes Simplex Virus, Japanese encephalitis Virus, West Nile Virus, Yellow Fever Virus and chimerics thereof, as well as Rhinovirus and Reovirus. It is within the knowledge of one skilled in the art to select an adherent host cell and the virus susceptible to this host and to use the method of the invention to obtain increased virus yield of the desired virus.

It is within the knowledge of one skilled in the art to select the respective microcarrier type, the microcarrier concentration in the starting culture, the adherent cells susceptible to the virus, and the medium and optimal growth conditions, like oxygen concentration, supplements of the medium, temperature, pH, pressure, steering speed and feeding control, to obtain a confluent cell culture biomass which can be used to obtain a cell biomass having increased cell density and microcarrier concentration according to this method. The cell culture having higher cell density biomass can be used then for effective virus propagation and production. After the cell culture has reached confluency, the method of the invention allows to obtain a cell culture having an increased cell density of microcarrier concentration of at least 1,3- fold up to 10 fold and obtain higher virus yield per culture volume due i) reduced culture volume and ii) increased productivity per cell.

The virus production process and the time span for production depend on the system used. The maximal virus yield reachable in the respective system can be determined by standard methods. When maximal virus production yield is reached, the virus and/or cells comprising the virus are harvested. The method of the invention, therefore, further comprises a step of harvesting the virus propagated and produced.

Another aspect of the invention provides for a method for production of purified virus or virus antigen comprising the steps of providing a culture of adherent cells bound to a microcarrier, growing the cell culture to confluence, infecting the culture of cells with a virus, wherein the cell density in the cell culture is increased (i) prior to infection with the virus or (ii) after infection with the virus, incubating said culture of cells infected with said virus to propagate said virus (f) harvesting the virus produced and (g) purifying said virus harvested.

Dependent on the nature of the virus used for infection and propagation, the virus produced is either found in the supernatant of the cell culture and/or associated with the cellular biomass. Lytic viruses, such as Influenza virus, lyse the cells after appropriate time after infection and the virus is released into the cell culture medium. The virus produced and released in the cell culture medium can be separated from the cellular biomass or other cell fragments by conventional methods, such as centrifugation, including ultracentrifugation, density gradient centrifugation, microfiltration, ultrafiltration, ion exchange chromatography etc. and purified.

Non-lytic viruses propagate within the cells and are still associated with the cells of the biomass. These viruses can be harvested by collecting the biomass, lysing the cells by conventional methods, such as treating the cells with a detergent, heat, freeze/thawing, sonication, French-press or other cell lysing methods. The viruses released from the cells are harvested, concentrated and purified. The purification of the virus can be done by any method known in the art, such as ultrafiltration, ion exchange chromatography or isopygnic centrifugation etc.

Influenza virus can be propagated on cell lines, including the most efficient MDCK cells, as well as on the cell line that has been licensed for use in the manufacture of human vaccines, Vero cells. Large scale production of Influenza virus in serum free or serum free and protein free medium on a mammalian cell culture on microcarrier beads in a bioreactor and the development of a Influenza virus vaccine has been described (Merten et al., 1999, Dev. Biol. Stand. 98: 23-37; Kistner et al., 1998. Vaccine 16:960-968; Kistner et al. 1999, Dev. Biol. Stand. 98:101-110 and WO 96/15231.

According to one aspect, the invention provides for a method for production of Influenza virus, comprising the steps of providing a culture of adherent cells bound to a microcarrier, growing the cell culture to confluence, infecting the cells with an Influenza virus, wherein the cell density in the cell culture is increased (i) prior to infection with the virus or (ii) after infection with the virus, incubating the culture of cells infected with said Influenza virus to propagate the virus. The cells infected with Influenza virus can be VERO or MDCK cells, or any cell that is susceptible to Influenza virus. According to a preferred embodiment of the invention, VERO cells are used and infected with Influenza virus. According to a preferred embodiment, the VERO cells are grown in serum free or serum and protein free medium from the original ampoule to the biomass. The VERO cells bound to the microcarrier are grown in the respective medium to confluence and cell density and microcarrier concentration is increased at least 1,3 fold. The cells can be infected with Influenza virus either prior or after increase of cell density of culture volume. After incubation of the infected high cell density biomass and production of virus, the Influenza virus or Influenza virus antigen produced is harvested. The harvested virus is further purified by a method known in the art, such as described in Kistner et al. 1998 (supra) or U.S. Pat. No. 6,048,537.

Another aspect of the invention provides for a cell culture biomass of adherent cell bound to microcarrier having high cell density, wherein the cell density biomass of the cells in the cell culture is at least 1,3-fold compared to a cell culture that has been grown to confluence. The culture of adherent cells bound to a microcarrier are cells selected from the group of anchorage-dependent cells of VERO, BHK, CHO, RK, RK44, RK13, MRC-5, MDCK, CEF or diploid monolayer cells. The cell culture biomass having high cell density is preferably a culture of VERO cells.

According to a preferred embodiment of the invention the cell culture biomass is grown in serum free medium and does not comprise any substances or agents derived from serum. According to another preferred embodiment the biomass is serum and protein free and does not comprise any serum derived substances or proteins added to the medium. Preferably, the cells have been grown in serum free or serum and protein free medium from the original ampoule to the biomass. The biomass having high cell density is maintained in serum free or serum and protein free medium during virus propagation and production process.

According to another embodiment of the invention the cells of the biomass having higher cell density compared to the cell culture that has been grown to confluence are infected with a virus. The cell density and volume of the culture medium of the high cell density biomass infected with virus is maintained during the virus propagation process.

Another aspect of the invention provides for a cell culture biomass of VERO cells bound to a microcarrier, wherein the biomass and the cell density of the VERO cells in said cell culture is at least 1,3-fold compared to a VERO cell culture that has been grown to confluence. The cell culture has also a higher microcarrier concentration compared to the cells gown to confluence.

According to a preferred embodiment of the invention the cell culture biomass having higher cell density is a biomass of VERO cells. Preferably, the cells are grown in serum free medium and the biomass is serum free. According to another preferred embodiment of the invention the biomass culture is serum and protein free.

Another aspect of the invention provides for a cell culture biomass of a cell culture of adherent cells bound to a microcarrier infected with a virus, wherein the biomass of the infected cells in said cell culture is at least 1,3-fold compared to a cell culture that has been grown to confluence prior to infection, and has higher cell density. According to one embodiment the cell culture biomass of cells is serum free. According to another preferred embodiment of the invention the cell culture biomass is serum and protein free. The cells are preferably VERO cells. This cell density of the high cell density biomass infected with virus is not decreased during the virus propagation process.

Another aspect of the invention provides for a cell culture biomass of VERO cells bound to microcarrier and having a high cell density bound to a microcarrier, wherein the biomass of the VERO cells in said cell culture is at least 1,3-fold compared to a VERO cell culture that has been grown to confluence, wherein the VERO cells are infected with virus. The VERO cells are infected with a virus selected from the group of Influenza virus, Ross River Virus, Hepatitis A Virus, Vaccinia Virus and recombinant derivatives thereof, Herpes Simplex Virus, Japanese encephalitis Virus, West Nile Virus, Yellow Fever Virus and chimeric thereof, Rhinovirus and Reovirus.

According to one another aspect, the invention provides a cell culture biomass of VERO cells bound to microcarrier and having high cell density said cells being infected with a Influenza virus, wherein the biomass of the VERO cells in said cell culture is at least 1,3-fold compared to a VERO cell culture that has been grown to confluence.

According to one another aspect, the invention provides a cell culture biomass of VERO cells bound to microcarrier and having high cell density said cells being infected with a Ross River virus, wherein the biomass of the VERO cells in said cell culture is at least 1,3-fold compared to a VERO cell culture that has been grown to confluence.

According to one another aspect, the invention provides a cell culture biomass of VERO cells bound to microcarrier and having high cell density said cells being infected with a Hepatitis A virus, wherein the biomass of the VERO cells in said cell culture is at least 1,3-fold compared to a VERO cell culture that has been grown to confluence.

Having now generally described this invention, the same will be understood by reference to the following examples which are provided herein for purposes of illustration only and are not intended to be limiting unless otherwise specified.

EXAMPLE 1

Virus Antigen Production on Concentrated Vero Cell Biomass a) Growth of Cell Culture VERO cells (African Green Monkey, *Cercopthecus aethiops,* kidney) were used as a production cell line. The cells have been obtained from the American Type Cell Culture Collection, Rockville, Md. at a passage number 124 under the designation ATCC CCL 81. The cells were adapted to grow in serum free or serum and protein free medium as described in Kistner et al., 1998 (supra), WO 96/15231 or U.S. Pat. No. 6,100,061. For growth in serum free medium a basal DMEM HAM's F12 medium supplemented with inorganic salts, amino acids, sodium bicarbonate (2 g/l) and yeast or soy bean extract (0.1 to 10 g/l) is used. The working cell bank was prepared without the use of any animal derived medium components.

Cells of the working cell bank were expanded in T-flasks and roller bottles with a split ratio of 1:6 or 1:8. Further propagation of the cells was performed in a 100 l stirred tank bioreactor using Cytodex® microcarrier as attachment substrate. The cells were grown at 37° C. for 6-8 days. The culture conditions of oxygen saturation 20%±10% and pH7.25±0.35 were kept constant. At the end of biomass production when cell have reached confluence growth, one part of the biomass reactor volume was concentrated two-fold by sedimentation and the cell density of the unconcentrated and concentrated cell culture was determined.

b) Determination of Cell Density of Biomass

The cell number of the biomass of the cell culture at the end of biomass production was determined either by trypsinization of the cells and counting with a CASY® cell counter (method A) as described by Scharfe et al. (1988. Biotechnologie in LaborPraxis 10:1096-1103) or by citric acid and crystal violet treatment followed by counting with a haemocytometer (method B) as described by Sanford et al. (1951. J. Natl. Cancer Inst. 11:773-795). The cell density and carrier concentration for Vero cells at the end of biomass production and after concentration of the confluent biomass (prior infection) were calculated by method A and B. The data are shown in Table 1.

TABLE 1

Determination of cell number in a confluent cell culture at the end of biomass production and after concentration of confluent cell culture

| | Biomass production | Concentrated Biomass |
|---|---|---|
| Carrier Concentration g/l | 5.0 | 10.0 |
| Cell Density cells/ml (method A) | $4.6 \times 10^6$ | $9.2 \times 10^6$ |
| Cell Density cells/ml (method B) | $5.6 \times 10^6$ | $11.2 \times 10^6$ |

EXAMPLE 2

Comparison of Virus Antigen Production of a Confluent Biomass and a Concentrated Confluent Biomass Vero cells with a defined passage number were thawed from liquid nitrogen and passaged in roux and roller bottles to produce sufficient cells to inoculate a 1.5 liter bioreactor. After reaching confluency with a final cell density of $1.5 \times 10^6$ cells/ml the cells were trypsinized and transferred to a 10 liter bioreactor. This in turn is used as an inoculum for a 100 liter bioreactor having a microcarrier concentration of 1.5 g/l. Starting from a working cell bank ampoule containing 1 cells about 30 generations are needed to reach the final confluent Vero cell biomass. The culture was grown to reach confluency with a final cell density of $1.9 \times 10^6$/ml. Prior to virus infection, two 10 liter bioreactor systems were loaded with cell culture biomass, having different total cell numbers. Fermenter A is loaded with $1.9 \times 10^{10}$ cells, and fermenter B with a total cell number of $3.8 \times 10^{10}$. To achieve higher biomass and carrier concentration to load fermenter B the cell culture grown to confluency was concentrated by sedimentation of the biomass to reach a two-fold concentration. Fermenter A contains 100% and fermenter B 200% cell biomass of the original cell culture grown to confluency.

a) Production of Influenza Virus

The cell culture in fermenter A and B were infected with Influenza virus strain H3N2 A/Sydney/5/97 with a m.o.i of 0.01. Identical process parameters of 32° C., $pO_2$ of 20% and pH 7.1 were applied. To activate Influenza virus for virus propagation a protease, such as trypsin, pronase or a trypsin-like part thereof, was added.

The virus antigen productivity of the two different cell cultures of fermenter A and B containing different biomass concentrations was determined and compared on the basis of Influenza virus titer (HAU/ml) and the antigen content (density gradient purified antigen). The peak area corresponds to the total antigen concentration at the end of the lytic cycle at day 3 after infection. The data is shown in Table 2.

TABLE 2

Determination of Influenza Virus titer and antigen in a confluent VERO cell culture and concentrated confluent VERO cell biomass

| | Fermenter | |
|---|---|---|
| | A | B |
| Carrier Concentration | 1.5 g/l | 3.0 g/l |
| Cell Density cells/ml (method B) | $1.90 \times 10^6$ | $3.80 \times 10^6$ |
| HAU/ml | 640 | 2560 |
| Peak Area (rel. Units) | 83.3 (100%) | 412.3 (495%) | b) Production of Ross River Virus

VERO cells were propagated as described above to confluency with a final density of $1.6 \times 10^6$ cells/ml. Prior to virus infection two 50 l bioreactor systems were loaded with cell culture biomass, having different total cell numbers. Fermenter A is loaded with $1.6 \times 10^6$ cell/ml, and fermenter B with $2.3 \times 10^6$ cells/ml, which is a 1,5 fold concentration of c confluent cell culture biomass. Fermenters A and B were infected with Ross River Virus and virus antigen productivity of fermenter A and B were determined as described above. Table 3 shows the results of virus yield obtained by using different concentrations of biomass for virus propagation.

TABLE 3

Determination of Ross River Virus titer and antigen production

| | Fermenter | |
|---|---|---|
| | A | B |
| Carrier Concentration g/l | 1.5 | 2.25 |
| Cell Density ($\times 10^6$ cells/ml) | 1.6 | 2.3 |
| Virus titer (log $TCID_{50}$) | 8.71 | 8.95 |

TABLE 3-continued

Determination of Ross River Virus titer and antigen production

| | Fermenter | |
|---|---|---|
| | A | B |
| Virus titer pfu/$10^6$ cells (×$10^6$) | 321 | 388 |
| Yield (%) | 100 | 121 |

EXAMPLE 3

Virus Antigen Production on Concentrated Biomass of RK-cells a) Growth of Cell Culture Rabbit kidney cells RK-13 or a complementing derivative thereof RK-D4R-44 as described by Holzer et al. (1997. J. Virol. 71:4997-5002) were used as production cell lines. Cells were grown in conventional medium containing 2% serum.

Cells from the working cell bank were expanded in T-flasks and roller bottles with a split ratio of 1:6. Further propagation of the cells was done in a 10 l stirred tank bioreactors using Cytodex® (Pharmacia) microcarriers as attachment substrate.

b) Production of Defective Vaccinia Virus

After the RK-13 or RK-D4R-44 cells have reached confluence and final cell density in the tank bioreactors, the biomass was infected with Vaccinia Virus WR or defective Vaccinia Virus vD4-ZG#2 as described by Holzer et al. 1997 (supra) with a m.o.i. of 0.01. After infection, two 10 l bioreactor systems were loaded with the infected cell culture biomass, having different total cell numbers. Fermenter A is loaded with $1.2 \times 10^{10}$, and fermenter B with a $2.4 \times 10^{10}$. To achieve higher biomass and carrier concentrations for fermenter B, the infected cell culture grown to confluence was concentrated by sedimentation of the biomass to reach higher concentration. Fermenter A contains 100% and fermenter B 200% cell biomass of the original cell culture grown to confluence. The virus antigen productivity of the two different cell culture fermenters A and B containing different biomass concentrations per volume of medium of infected cells was determined. The results are summarized in Table 4.

TABLE 4

Determination of Vaccinia Virus titer on RK-cells

| | Fermenter | |
|---|---|---|
| | A | B |
| Carrier Concentration g/l | 1.5 | 2.5 |
| Cell Density (×$10^6$ cells/ml) | 1.2 | 2.4 |
| Virus titer pfu/$10^6$ cells (×$10^6$) | 0.8 | 1.3 |
| Yield (%) | 100 | 162 |

The above examples are provided to illustrate the invention but not to limit its scope. Other variants of the invention will be readily apparent to one of ordinary skill in the art and are encompassed by the appended claims. All publications, patents, and patent applications cited herein are hereby incorporated by reference for all purposes.

What is claimed is:

1. A concentrated cell culture biomass prepared by growing a cell culture of adherent cells bound to a microcarrier to confluence, and then concentrating the cell culture, wherein cell density and microcarrier concentration of the concentrated cell culture biomass is at least 1.3 fold compared to cell density and microcarrier concentration of said cell culture grown to confluence.

2. The culture according to claim 1 wherein said cells are VERO cells.

3. The culture according to claim 1 wherein said culture is serum free.

4. The culture according to claim 1 wherein said culture is serum and protein free.

5. The culture according to claim 1 wherein said cells are infected with a virus.

6. The culture of claim 5 wherein cell density of the biomass of the infected cells in said cell culture is at least 1.3-fold compared to cell density of said cell culture grown to confluence prior to infection.

7. The cell culture according to claim 5 infected with a virus selected from the group consisting of Influenza virus, Ross River Virus, Hepatitis A Virus, Vaccinia Virus, recombinant Vaccinia Virus, Herpes Simplex Virus, Japanese encephalitis Virus, West Nile Virus, Yellow Fever Virus, chimeric Yellow Fever Virus, Rhinovirus and Reovirus.

8. The cell culture biomass of claim 7 wherein the virus is Influenza virus.

9. The cell culture biomass of claim 7 wherein the virus is Ross River virus.

10. The cell culture biomass of claim 7 wherein the virus is Vaccinia virus.

* * * * *